United States Patent [19]

Camaggi et al.

[11] Patent Number: 5,314,879
[45] Date of Patent: May 24, 1994

[54] SILANYL OXYPROPYLAMINES ENDOWED WITH ANTIFUNGAL ACTIVITY

[75] Inventors: Giovanni Camaggi, Novara; Lucio Filippini, Saronno; Marilena Gusmeroli, Monza; Carlo Garavaglia, Cuggiono; Luigi Mirenna, Milan, all of Italy

[73] Assignee: Ministero Dell 'Universita' E Della Ricerca Scientifica E Tecnologica, Rome, Italy

[21] Appl. No.: 661,935

[22] Filed: Feb. 28, 1991

[30] Foreign Application Priority Data

Mar. 2, 1990 [IT] Italy ............................... 19540 A/90

[51] Int. Cl.$^5$ ...................... A01N 55/00; C07F 7/10; C07F 7/18
[52] U.S. Cl. ......................................... 514/63; 544/59; 544/69; 544/174; 544/122; 544/124; 544/335; 546/14; 546/334; 548/205; 548/235; 548/247; 549/75; 556/445; 556/486; 564/374
[58] Field of Search .................... 544/59, 60, 62, 69, 544/116, 122, 123, 124, 128, 133, 135, 137, 146, 174; 514/227.5, 227.8, 228.2, 233.5, 233.8, 234.5, 235.5, 235.8, 236.8, 239.2, 63; 546/14; 556/407, 408, 445, 486

[56] References Cited

U.S. PATENT DOCUMENTS 4,628,048 12/1986 Acker et al. .................... 544/69
4,837,236 6/1989 Meki et al. ................... 514/233.8
5,135,955 8/1992 Campbell et al. ............... 514/654

FOREIGN PATENT DOCUMENTS 2020016 12/1990 Canada.
0262870 4/1988 European Pat. Off..
0339878 2/1989 European Pat. Off..
0405440 1/1991 European Pat. Off..
64-6245 1/1989 Japan.

OTHER PUBLICATIONS

Campbell et al., Chemical Abstract vol. 112, No. 178319e (1989).
Abstract —Benzylamine Derivative, Production Thereof and Germicide Containing Said Derivative as Active Ingredient, JP-64-6245 published Jan. 10, 1989, Sumimoto Chemical Co.
European Search Report, Place of Search: Vienna, Dated: Dec. 15, 1992, EP 91103131.8, Examiner Korber.
"Comparative Study of the Inhibition of Sterol Biosynthesis in Rubis Fruticosus Suspension Cultures and Zea Mays Seedlings by N-(1,5,9-Trimethyldecyl)-4α,10-Dimethyl-S-Aza-Trans-Decal-3β-ol and Derivatives", Taton, et al., Phytochemistry, vol. 26, No. 2, pp. 385-392, 1987.
"Inhibition of Sterol $\Delta^8 \rightarrow \Delta^7$-Isomerase and $\Delta^{14}$-Reductase by Fenpropimorph, Tridemorph and Fenpropidin in Cell14 Free Enzyme Systems from Saccharomyces Cerevisiae", Baloch, et al., Phytochemistry, vol. 26, No. 3, pp. 663-668, 1987.
"Inhibition of $\Delta^8 \rightarrow \Delta^7$-Sterol Isomerase and of Cyclo-Eucalenol-Obtusifoliol Isomerase by N-Benzyl-8-AZA-4α, 10-Dimethyl-Trans-Decal-3β-ol, An Analogue of a Carbocationic High Energy Intermediate" Rahier, et al., Phytochemistry, vol. 24, No. 6, pp. 1223-1232, 1985.

Primary Examiner—Mukund J. Shah
Assistant Examiner—Philip I. Datlow
Attorney, Agent, or Firm—Morgan & Finnegan

[57] ABSTRACT

The invention relates to the manufacture and use of aryl-propyl-aminic compounds having the following formula

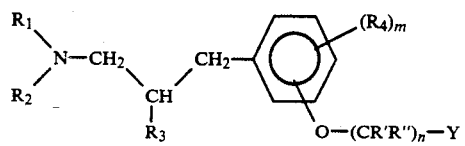

that have a high antifungal activity and are useful in the agricultural field as fungicides.

9 Claims, No Drawings

SILANYL OXYPROPYLAMINES ENDOWED WITH ANTIFUNGAL ACTIVITY

DESCRIPTION OF THE INVENTION

The present invention relates to aryl-propyl-aminic compounds endowed with a high antifungal activity, to the process for producing them and to their use in the agricultural field as fungicides.

Therefore, the object of the present invention are the compounds having the general formula:

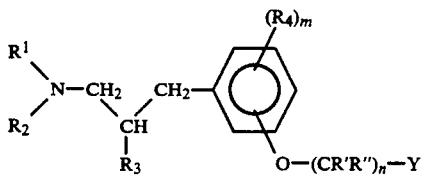

wherein:
$R_1$ and $R_2$, which may be either equal to, or different from, each other, represent H atoms, either linear or branched $(C_1-C_6)$-alkyl groups, Ar-B groups in which
Ar is a $(C_6-C_{10})$-aryl or $(C_6-C_{10})$-halo-aryl group and B is a $(C_1-C_4)$-alkylene or $(C_1-C_2)$-alkyl-$(C_1-C_4)$-alkylene group,
or, taken together with each other and together with the N atom, Ar and B represent a $(C_3-C_8)$-heterocyclic group or a $(C_2-C_7)$-heterocyclic group containing a second heteroatom selected from among O and S, with said heterocyclic groups being optionally substituted with one or more $(C_1-C_4)$-alkyl groups, $(C_6-C_{10})$-aryl groups, Ar-B groups as defined above, and halogens;
$R_3$ represents a $(C_1-C_3)$-alkyl group;
$R_4$ which, when m is higher than 1, may be either different from, or equal to, one another, represent halogen atoms, $(C_1-C_3)$-alkyl groups or $(C_1-C_3)$-halo-alkyl groups;
m is an integer comprised within the range of from 0 to 4;
R', R", which may be either equal to, or different from, each other, represent H, $(C_1-C_3)$-alkyl group, halogen atoms;
n is an integer comprised within the range of from 0 to 3;
y represents a $-CH=CH_2$ (ethenyl) group, a $(C_3-C_6)$-cycloalkyl group, a 5- or 6-membered heterocyclic group, while said groups can be optionally substituted with one or more halogen atoms, $(C_1-C_4)$-alkyl groups, $(C_1-C_2)$-haloalkyl groups, $(C_1-C_3)$-alkoxy groups, $(C_1-C_3)$-halo-alkoxy groups; or represents a

group in which
C, D, E, either equal to, or different from, one another, represent H atoms, $(C_1-C_4)$-alkyl groups, $(C_1-C_4)$-haloalkyl groups, $(C_1-C_4)$-alkoxy groups, $(C_1-C_4)$-halo-alkoxy groups, $(C_6-C_{10})$-aryl groups, and $(C_6-C_{10})$-haloaryl groups.

The compounds of general formula (I) contain at least one center of asymmetry: the synthesis and use of pure enantiomers or of pure diastereoisomers, as well as mixtures thereof in any ratios, falls within the scope of the instant invention.

In the disclosure of the instant invention, by "halogens" atoms of F, Cl, Br and I are meant.

Examples of aryl groups are the phenyl group, the naphthyl group and higher homologues.

Examples of Ar-B groups are benzyl and 3-phenyl-propyl.

Examples of

groups, when $R_1$ and $R_2$, together with each other, represent a $(C_3-C_8)$- or $(C_2-C_7)$-heterocyclic group as defined hereinabove, are those groups which derive from morpholine, 2,6-dimethyl-morpholine, piperidine, 2,6-dimethylpiperidine, thiomorpholine, and so forth. They can also be substituted as defined above.

Examples of 5- or 6-membered heterocyclic Y groups are: pyridines, pyrimidines, thiophenes, thiazoles, oxazoles, isooxazoles and their derivatives containing a fused benzene ring, and containing such substituents as defined above.

Among the Y groups with the meaning of $(C_3-C_6)$-cycloalkyl groups, the cyclohexyl, cyclopropyl, cyclopentyl, cyclobutyl groups, also substituted as defined above, such as 1-methyl-2,2-dichloro-cyclopropyl, may be mentioned.

Among the silyl groups, trimethyl-silyl, tert.-butyl-dimethyl-silyl and dimethyl-phenyl-silanyl groups may be mentioned.

The following are further objects of the present invention:

the salts of the compounds of general formula (I) deriving from an inorganic acid, such as a hydrogen halide acid, for example: hydriodic, hydrobromic, hydrochloric acids: sulfuric acid, nitric acid, thiocyanic acid and phosphoric acid; or from an organic acid, such as acetic acid, propanoic acid, ethane-dicarboxy acid, propane-dicarboxy acid, benzoic acid, salicylic acid, saccharin, methane-sulfonic acid, 4-methyl-benzene-sulfonic acid, and so forth, according to well-known techniques;

the metal complexes obtained by the complex-forming reaction between the derivatives of (I) type with an either organic or inorganic metal salt such as a halide, a nitrate, a sulfate, a phosphate, e.g., of copper, manganese, zinc or iron, according to well-known techniques.

The compounds falling within the scope of the general formula (I) can be prepared by substantially known, i.e., conventional methods, which can anyway be carried out by different alternative routes.

A preferred method can be schematically represented as follows (for n=1):

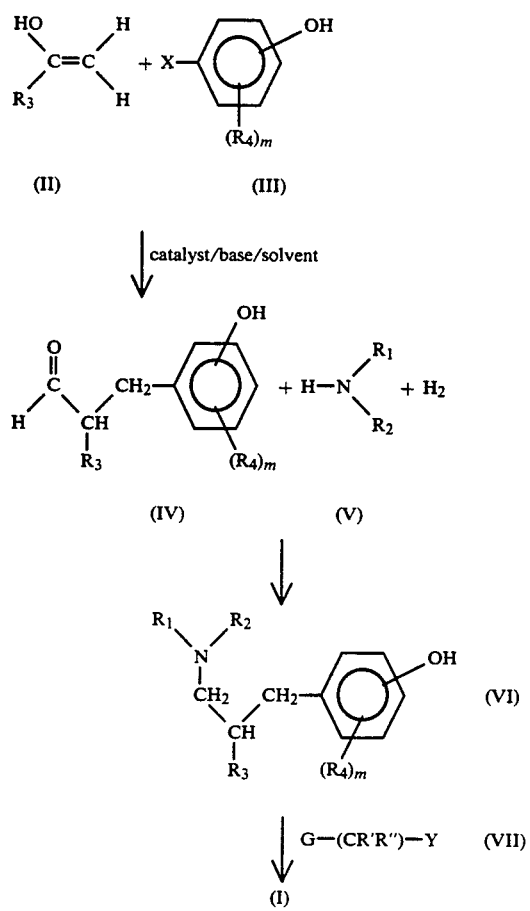

In a more explicit way, the allyl alcohol (II) is reacted with the phenol (III), wherein X means a halogen (Br, I), or an activated ester (trifluoromethane-sulfonic ester), in the presence of a Pd-(II) salt [Pd-(II) chloride, Pd-(II) acetate]and an organic base (triethylamine, tributylamine) or inorganic base (sodium bicarbonate, potassium bicarbonate), in a dipolar protic (water, ethanol) or aprotic solvent (N,N-dimethyl-formamide, N-methyl-pyrrolidone), or mixtures of such solvents, at a temperature comprised within the range of from 0° C. to about the boiling temperature of the solution.

The addition of phosphines such as tris-(ortho-tolyl)-phosphine or triphenylphosphine may prove itself as advantageous (see JOC 41 1206, 1976).

The aldehyde (IV.) is obtained and after the addition of the amine (V) is hydrogenated in situ to yield the aminic compound (VI). The addition of a usual hydrogenation catalyst (Pd supported on charcoal, Raney-nickel) may prove advantageous. Hydrogen pressure can be comprised within the range of from 1 to 10 atmospheres, and the temperature can be comprised within the range of from about 0° C. to about 60° C. (see J. March "Advanced Organic Chemistry", 2nd Edition, Int. St. Edition, page 819).

In the preparation diagram reported above, the symbols $R_1$, $R_2$, $R_3$, $R_4$, R', R", Y and m have the previously defined meanings.

By reacting the amine (VI) with the compound (VII), the compound (I) is obtained. In compound (VII), G stands for halogen (Cl, Br, I) or activated ester (methane-sulfonic ester, p-toluene-sulfonic ester). The reaction is carried out in the presence of an either organic (triethylamine, pyridine), or inorganic base (sodium carbonate, sodium bicarbonate), in dipolar protic (water, ethanol) or aprotic solvents (N,N-dimethyl-formamide, N-methyl-pyrrolidone), at temperatures comprised within the range of from 25° C. to the boiling temperature of the solution (see J. March "Advanced Organic Chemistry", 2nd Edition, Int. St. Edition, page 357).

If desired, from the compounds (I) the corresponding metal salts and/or complexes can be prepared according to well-known techniques.

The alcohols (II) and phenols (III) are in general easily available from the market, or can be prepared according to known techniques.

The compounds (VII) are easily available from the market; in the event that the symbol Y means $$-\underset{E}{\overset{C}{\underset{|}{Si}}}-D$$

and at least one of the C, D, E is ($C_1$–$C_4$)-perfluoroalkyl group the compound (VII) can be obtained according to methods known from literature [JACS 73 3518 (1951), Te. Le. 25, 2195 (1984)].

The amines (V) are products available from the market, or they can be easily obtained by synthesis (see J. March "Advanced Organic Chemistry", 2nd Edition, Int. St. Edition, page 357).

The compounds of general formula (I) are endowed with high activities as inhibitors of the growth of several species of pathogen fungi which attack the cultivations of useful plants.

When they are applied to useful plants or to parts of useful plants, such as, e.g., to leaves, the compounds of formula (I) show both a preventive and a curative activity, and have proved themselves to be particularly effective in preventing the diseases caused by pathogen fungi, such as, e.g., those belonging to Erysiphe and Helminthosporium genera.

Examples of plant diseases which can be combated by the compounds according to the present invention are the following:

*Erysiphe graminis* on cereals,
*Sphaeroteca fuliginea* on Cucurbitaceae (e.g., cucumber),
*Puccinia* on cereals,
*Septoria* on cereals,
*Helminthosporium* on cereals,
*Rhynchorium* on cereals,
*Podosphaera leucotricha* on apple-tree,
*Uncinula necator* on vines,
*Venturia inaegualis* on apple-tree,
*Pyricularia oryzae* on rice,
*Botrytis cinerea*,
*Fusarium* on cereals,
And still other diseases.

For practical uses in agriculture, it is often useful to have available antifungal compositions containing one or more components of formula (I) as active substances.

The application of these compositions may take place on each part of the plant, such as, e.g., leaves, stems, branches and roots, or on the same seeds, before seeding, or also on the soil on which the plant grows. The compositions can be used in the form of dry powders, wettable powders, emulsifiable concentrates, pastes, granulates, solutions, suspensions, and the like: the selection of the type of composition will depend on the specific use.

The compositions are prepared in a known way, for example either diluting or dissolving the active substance with a solvent medium and/or a solid diluent, possibly in the presence of surfactants. As solid diluents, or supports, the following may be used: silica, kaolin, bentonite, talc, fossil meal, dolomite, calcium carbonate, magnesium oxide, gypsum, clays, synthetic silicates, attapulgite, sepiolite.

The liquid diluents may be, of course beside water, various types of solvents, such as, e.g., aromatic solvents (benzene, xylenes or mixtures of alkyl-benzenes), chloroaromatic compounds (chlorobenzene), paraffins (petroleum cuts), alcohols (reethanol, propanol, butanol), amines, amides (dimethylformamide), ketones (cyclohexanone, acetophenone, isophorone, ethyl-amyl-ketone), esters (isobutyl acetate).

As the surfactants, the following may be used: salts of sodium, calcium or triethanolamine of alkyl-sulfates, alkyl-sulfonates, alkyl-aryl-sulfonates, polyethoxylated alkyl-phenols, adducts of ethylene oxide on fatty alcohols, polyethoxylated fatty acids, polyethoxylated sorbitol esters, polyethoxylated fats, ligno-sulfonates.

The compositions may also contain special additives for particular purposes, such as, e.g., bonding agents as gum arabic, polyvinyl alcohol, polyvinylpyrrolidone.

If so desired, to the compositions according to the present invention, also other active substances such as fungicides, plant growth regulants, herbicides, insecticides, fertilizers can be added.

The concentration of active substance in above said compositions may be comprised within a wide range, as a function of the active compound, of the culture, of the pathogen agent, of environmental conditions and of the type of formulation adopted. In an at all general way, the concentration of active substance will be comprised within the range of from 0.1% to 95% and preferably of from 0.5% to 90% (all percentages by weight).

EXAMPLES

The following Examples illustrate the invention.

Example 1

(a) Synthesis of
4-{3-[4-(trimethylsilylmethoxy)-phenyl]-2-methyl-propyl}-2,6-dimethyl-morpholine (Compound No. 1)

1 g of 4-[3-(4-hydroxy-phenyl)-2-methylpropyll-2,6-dimethyl-morpholine is dissolved in 10 cc of dimethylformamide. To the resulting solution 0.7 g of anhydrous sodium carbonate is added, the resulting mixture is heated to 80° C. under a nitrogen blanketing atmosphere, and is kept heated at this temperature for 30 minutes. Then 0.6 g of potassium iodide and 0.65 g of chloromethyl-trimethyl-silane are added and the heating of the mixture is continued for a further 4 hours. The reaction mixture is poured in water and is submitted to an extraction with ethyl ether. The ethereal extract is then thoroughly dehydrated and evaporated under a reduced pressure. The resulting raw product is purified by chromatography on silica gel, with hexane/ethyl acetate=9:1 as the eluent. 0.5 g of compound 1 is obtained.

| Analysis: nmr (60 Mhz) in CDCl$_3$: |
|---|
| δ = 6.7 (4H, m) |
| = 3.5 (4H, m) |
| = 0.8–2.6 (18H, m) |
| = 0.0 (9H, s) |

(b) Synthesis of
4-[3-(4-(hydroxy-phenyl)-2-methylpropyl]-2,6-dimethyl-morpholine used as the starting product 1.1 g of p-iodo-phenol is added to a solution of betamethallyl alcohol (0.6 9) in 20 cc of deionized water and 2.5 cc of N-methyl-pyrrolidone. The solution is purged with nitrogen, and then potassium carbonate (2.07 g) and palladium acetate (0.011 g) are added. The resulting mixture is heated to 80° C. and is kept at this temperature for 10 hours. Then 2,6-dimethyl-morpholine (1.8 g) is added and the atmosphere inside the reaction vessel is replaced by hydrogen (1.5 atm.), with the reaction mixture being kept vigorously stirred at a temperature of 40° C. When the reaction is complete, the reaction mixture is extracted with methylene chloride, the extract is thoroughly dehydrated and is evaporated under reduced pressure.

The resulting raw product is purified by chromatography on silica gel, with hexane/ethyl acetate=3:2 as the eluent. 0.9 g of desired compound is obtained.

| Analysis: nmr (60 Mhz) in CDCl$_3$ : |
|---|
| δ = 6.7 (4H, m) |
| = 5.1 (1H, s) |
| = 3.5 (2H, m) |
| = 0.8–2.6 (18H, m) |

Example 2

By operating in a similar way, starting from the corresponding raw materials, the compounds 2-11 were synthetized. The analytical characteristics of such compounds, determined by N.M.R., are also reported.

| Compound No. 2 4-{3-[3-(2-(4,6-dichloro)-pyridyloxy)-phenyl]-2-methylpropyl}-2,6-dimethyl-morpholine. nmr (60 Mhz) in CDCl$_3$: |
|---|
| δ = 7.9 (1H, d) |
| = 7.7 (1H, d) |
| = 6.9 (4H, m) |
| = 3.6 (2H, m) |
| = 0.8–2.8 (18H, m) |
| Compound No. 3 4-{3-[3-(2-(4-nitro)-pyridyloxy)-phenyl]-2-methylpropyl}-2,6-dimethyl-morpholine. nmr (60 Mhz) in CDCl$_3$: |
| δ = 8.9 (1H, d) |
| = 8.3 (1H, dd) |
| = 6.9–7.0 (5H, m) |
| = 3.5 (2H, m) |
| = 0.8–2.8 (18H, m) |
| Compound No. 4 4-{3-[3-(cyclopentyloxy)-phenyl]-2-methylpropyl}-2,6-dimethyl-morpholine. nmr (60 Mhz) in CDCl$_3$: |
| δ = 7.1 (1H, t) |
| = 6.7 (3H, m) |
| = 4.7 (1H, m) |
| = 3.6 (2H, m) |
| = 0.8–3.0 (26H, m) |

-continued

Compound No. 5
4-{3-[3-(cyclopropylmethoxy)-phenyl]-2-methylpropyl}-2,6-dimethyl-morpholine.
nmr (60 Mhz) in CDCl₃ :

δ = 6.5–7.2 (4H, m)
= 3.6 (4H, m)
= 0.2–2.8 (23H, m)

Compound No. 6
4-{3-[3-(trimethylsilylmethoxy)-phenyl]-2-methylpropyl}-2,6-dimethyl-morpholine.
nmr (60 Mhz) in CDC;₃:

δ = 6.3–7.0 (4H, m)
= 3.6 (4H, m + s)
= 0.8–2.9 (18H, m)
= 0.0 (9H, s)

Compound No. 7
4-{3-[4-(2-(4,6-(dichloro)-pyridyloxy)-phenyl]-2-methylpropyl}-2,6-dimethyl-morpholine.
nmr (60 Mhz) in CDCl₃:

δ = 7.9 (1H, d)
= 7.7 (1H, d)
= 7.0 (4H, m)
= 3.6 (2H, m)
= 0.8–2.9 (18H, m)

Compound No. 8
4-{3-[4-(2-pyrimidyloxy)-phenyl]-2-methylpropyl}-2,6-dimethyl-morpholine.
nmr (60 Mhz) in CDCl₃:

δ = 8.5 (2H, d)
= 7.0 (5H, m)
= 3.6 (2H, m)
= 0.8–2.8 (18H, m)

Compound No. 9
4-{3-[4-(cyclopropyl-methoxy)-phenyl]-2-methylpropyl}-2,6-dimethyl-morpholine.
nmr (60 Mhz) in CDCl₃:

δ = 6.9 (4H, m)
= 4.7 (1H, m)
= 3.6 (2H, m)
= 0.8–2.8 (26H, m)

Compound No. 10
4-{3-[3-(cyclohexyl-methoxy)-phenyl]-2-methylpropyl}-2,6-dimethyl-morpholine.
nmr (60 Mhz) in CDCl₃:

δ = 6.4–7.1 (4H, m)
= 3.6 (4H, m)
= 0.6–2.8 (29H, m)

Compound No. 11
4-{3-[4-(tert.-butyl-dimethyl-silyl-oxy)-phenyl]-2-methylpropyl}-2,6-dimethyl-morpholine.
nmr (60 Mhz) in CDCl₃:

δ = 6.8 (4H, m)
= 3.6 (4H, m + s)
= 0.8–2.8 (27H, m)
= 0.0 (6H, s)

Example 3

Determination of the preventive fungicidal activity on *Helminthosporium teres*

Both faces of leaves of plants of barley cv. Ama, grown in pots in a conditioned atmosphere, were sprayed with the investigated products (Compounds Nos. 5 and 10) in water-acetonic solution at 20% of acetone (volume/volume).

After a stay of 2 days in an atmosphere conditioned at 20° C. and 70% R.H., both faces of the leaves of the plants were sprayed with an aqueous suspension of *Helminthosporium teres* (250,000 conidia/cc). After a stay of 24 hours in an atomsphere saturated with humidity, at 21° C., the plants were stored in a conditioned environment for fungus incubation.

At the end of said time (12 days), the severity of the infection was estimated visually, and scores were as- signed on the basis of a scale ranging from 100 (healthy plant) down to 0 (completely infected plant)

The data obtained is summarized in Table 1.

TABLE 1

| COMPOUND No. | DOSIS (ppm) | HELMINTHOSPORIUM CONTROL, % |
|---|---|---|
| 5 | 500 | 100 |
|  | 125 | 100 |
| 10 | 500 | 100 |
|  | 125 | 100 |

Example 4

Determination of the fungicidal activity on corn oidium (*Erysiphe graminis* D.C.)

Preventive Activity

Both faces of leaves of plants of corn cv. Irnerio, grown in pots in a conditioned environment, were sprayed with the investigated products (Compounds Nos. 1 and 9) in water-acetonic solution at 20% of acetone (volume/volume).

After a stay of 1 day in an atmosphere conditioned at 20° C. and 70% R.H., both faces of the leaves of the plants were sprayed with an aqueous suspension of *Erysiphe graminis* (200,000 conidia/cc). After a stay of 24 hours in an atmosphere saturated with humidity, at 21° C., the plants were stored in a conditioned atmosphere for fungus incubation.

At the end of said incubation time (12 days), the severity of the infection was estimated visually, and scores were assigned on the basis of a scale ranging from 100 (healthy plant) down to 0 (completely infected plant)

Curative Activity

Both faces of leaves of plants of corn cv. Irnerio, grown in pots in a conditioned atmosphere, were sprayed with an aqueous suspension of *Erysiphe graminis* (200,000 conidia/cc). After a stay of 24 hours in an atmosphere saturated with humidity, at 21° C., the leaves were sprayed with the investigated products (Compounds Nos. 1 and 9) in water-acetonic solution at 20% of acetone (volume/volume).

At the end of fungus incubation time (12 days), the severity of the infection was estimated visually, and scores were assigned on the basis of a scale ranging from 100 (healthy plant) down to 0 (completely infected plant)

The data obtained is summarized in Table 2.

TABLE 2

| COMPOUND No. | DOSIS (ppm) | ERYSIPHE CONTROL, % |
|---|---|---|
| 1 | 500 | 100 |
|  | 250 | 100 |
|  | 125 | 99 |
| 9 | 500 | 100 |
|  | 250 | 100 |
|  | 125 | 100 |

We claim:

1. Antifungal compounds useful in the agricultural field having the formula:

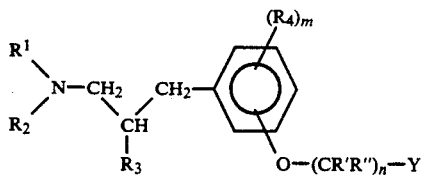

wherein:
- $R_1$ and $R_2$, which may be either equal to, or different from, each other, represent H atoms, either linear or branched $(C_1-C_6)$-alkyl groups,
  Ar-B groups in which Ar is a $(C_6, C_{10})$-aryl or $(C_6, C_{10})$-halo-aryl group and
  B is a $(C_1-C_4)$-alkylene or $(C_1-C_2)$-alkyl-$(C_1-C_4)$-alkylene group,
  or $R_1$ and $R_2$ taken together with the N atom form a $(C_3-C_8)$-heterocyclic group or a $(C_2-C_7)$-heterocyclic group containing a second heteroatom selected from among O and S, said heterocyclic groups being optionally substituted with one or more $C_1-C_4$ alkyl groups, $(C_6-C_{10})$-aryl groups, halogens, or Ar-B groups in which the symbols Ar and B have the same meanings are defined above;
- $R_3$ represents a $(C_1-C_3)$-alkyl group;
- $R_4$ which, when m is greater than 1, may be either different from, or equal to, one another, represent halogen atoms, $(C_1-C_3)$-alkyl groups or $(C_1-C_3)$-halo-alkyl groups;
- m is an integer within the range of from 0 to 4; R', R'', which may be either equal to, or different from, each other, represent H, $(C_1-C_3)$-alkyl group or halogen atoms;
- n is an integer within the range of from 0 to 3;
- Y represents a

group in which
C, D, E, either equal to, or different from, one another, represent H atoms, $(C_1-C_4)$ alkyl groups, $(C_1-C_4)$haloalkyl groups, $(C_1-C_4)$ alkoxy groups, $(C_1-C_4)$-halo-alkoxy groups, $(C_6,C_{10})$-aryl groups, and $(C_6, C_{10})$-haloaryl groups;

their enantiomers and diastereoisomers and corresponding metal salts and complexes.

2. A compound according to claim 1, wherein said $(C_3-C_8)$-heterocyclic group or a $(C_2-C_7)$-heterocyclic group is selected from among morpholinic, 2,6-dimethyl-morpholinic, piperidinic, 2,6-dimethyl-piperidinic, thiomorpholinic groups, with said groups optionally substituted with one or more halogen atoms, $C_1-C_4$ alkyl groups, $(C_6-C_{10})$-aryl groups, or Ar-B groups in which the symbols Ar and B have the same meanings as defined above.

3. Compounds according to claim 1, wherein said Ar-B group is selected from benzyl group and 3-phenyl-isopropyl group.

4. A compound according to claim 1, wherein said $(C_3-C_8)$-heterocyclic group or a $(C_2-C_7)$-heterocyclic group is substituted with at least one group selected from $C_1-C_4$ alkyl, $(C_6,C_{10})$-aryl groups, Ar-B groups in which the symbols Ar and B have the same meaning as defined above, and halogen atoms.

5. Compound according to claim 1, which is 4-{3-[4-(trimethylsilylmethoxy)-phenyl]-2-methylpropyl}-2,6-dimethyl-morpholine.

6. Compound according to claim 1, which is 4-{3-[3-(trimethylsilylmethoxy)-phenyl]-2,6-dimethyl-morpholine.

7. Compound according to claim 1, which is 4-{3-[4-(tert.-butyl-dimethyl-silyl-oxy)-phenyl]-2-methylpropyl}-2,6-dimethyl-morpholine.

8. An agricultural antifungal composition comprising the compounds of claim 1 in an agriculturally acceptable carrier.

9. A method of inhibiting fungi belonging to the class of Erysiphe and *Helminthosporium genera* comprising applying an effective amount of the composition of claim 8 to cultivars to inhibit the growth of the pathogen fungi belonging to Erysiphe and *Helminthosporium genera*.

* * * * *